(12) United States Patent
Dirix et al.

(10) Patent No.: US 8,287,784 B2
(45) Date of Patent: Oct. 16, 2012

(54) COMPOSITIONS AND METHODS OF MAKING COMPOSITIONS

(75) Inventors: Yvo Dirix, Erlenbach (CH); Lorenz Brunner, Zurich (CH); Jonathan Sander, Basel (CH)

(73) Assignee: Smith and Nephew Orthopaedics AG, Rotzkreuz (CH)

( * ) Notice: Subject to any disclaimer, the term of this patent is extended or adjusted under 35 U.S.C. 154(b) by 0 days.

(21) Appl. No.: 13/003,756

(22) PCT Filed: Jul. 10, 2009

(86) PCT No.: PCT/EP2009/005028
§ 371 (c)(1),
(2), (4) Date: Mar. 30, 2011

(87) PCT Pub. No.: WO2010/003688
PCT Pub. Date: Jan. 14, 2010

(65) Prior Publication Data
US 2011/0180948 A1    Jul. 28, 2011

(30) Foreign Application Priority Data
Jul. 11, 2008 (GB) .................................. 0812890.2

(51) Int. Cl.
B29C 43/02 (2006.01)
A61F 2/28 (2006.01)
C08F 2/46 (2006.01)

(52) U.S. Cl. ........ 264/126; 264/485; 264/488; 424/423; 522/161; 623/20.14; 623/22.11

(58) Field of Classification Search ........................ None
See application file for complete search history.

(56) References Cited

U.S. PATENT DOCUMENTS

| 2004/0156879 A1* | 8/2004 | Muratoglu et al. | 424/423 |
| 2004/0208902 A1 | 10/2004 | Gupta | |
| 2004/0212161 A1* | 10/2004 | Haigh | 280/47.1 |
| 2007/0059334 A1* | 3/2007 | Abt et al. | 424/423 |
| 2008/0036111 A1* | 2/2008 | Sun | 264/85 |

FOREIGN PATENT DOCUMENTS

| WO | 2005/121221 A1 | 12/2005 |
| WO | 2008/052574 A1 | 5/2008 |

OTHER PUBLICATIONS

Database WPI Week 200577 Thomson Scientific, London, GB; AN 2005-752230 XP002552037 & JP 2005 276747 A (Hitachi Ltd) Oct. 6, 2005 abstract (4 pages).
Chinese First Office Action issued in Chinese Application No. 200980127030, mailed May 17, 2012, 14 pages.

* cited by examiner

*Primary Examiner* — Mary F Theisen
(74) *Attorney, Agent, or Firm* — Krieg DeVault LLP

(57) ABSTRACT

A method for obtaining a composition of at least two components, comprising the steps of: providing at least one first fluid component; providing at least one second solid component and processing it so that the first component can diffuse into the second component; and diffusing the first component into the second component. A composition prepared by such a method.

51 Claims, 4 Drawing Sheets

Two fluid fronts that are opposite. First one side will be immersed than the second side Standing: Single side / one fluid front ∿∿∿ = level of soaking liquid Two fluid fronts that are perpendiclar, standing + flat Flat: One fluid front Examples of one or more soaking steps with different soaking directions.

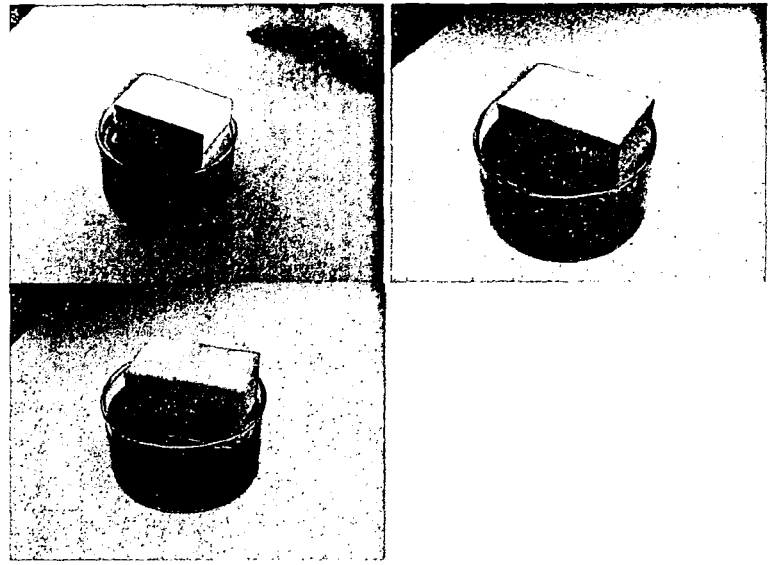
Figure 1: Soaking of a compacted GUR 1020 block in a red isopropanol/fuchsin solution. Left: seconds after immersion; middle 30 minutes after immersion, right 1 hr after immersion
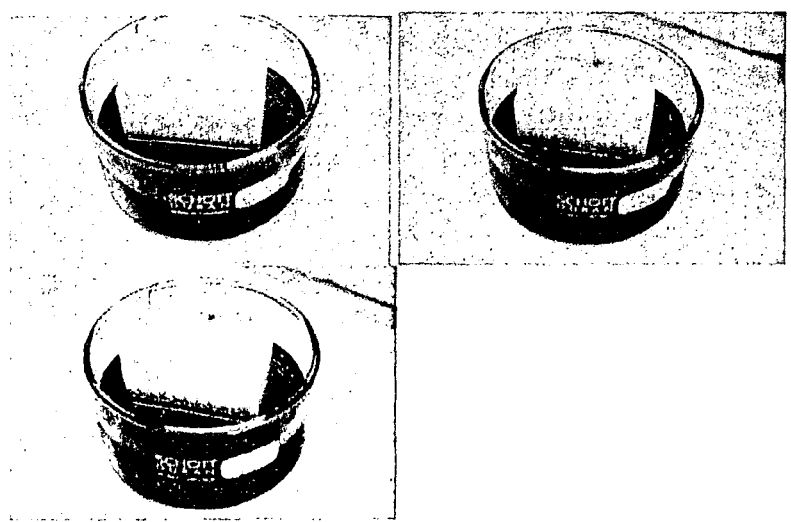
Figure 2: Soaking of a sintered GUR 1020 block in a red isopropanol/fuchsin solution. Left: seconds after immersion; middle 30 minutes after immersion, right 1 hr after immersion

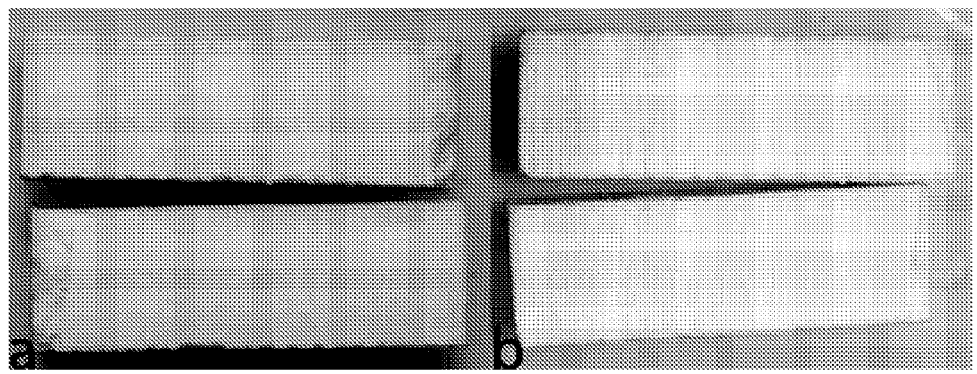
Figure 3: Compacted and soaked blocks cut into two pieces (1% curcumin solution in acetone) after drying. a) and b) represent two different blocks, both cut in 2 pieces
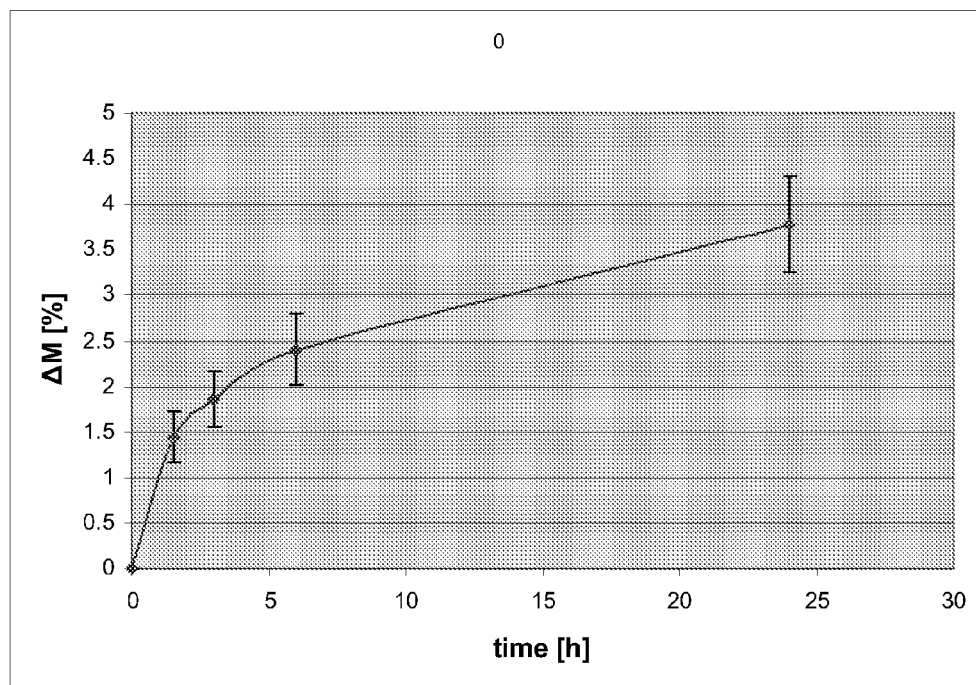
Figure 4: Average weight change of the 2 standing blocks as a function of the soaking time

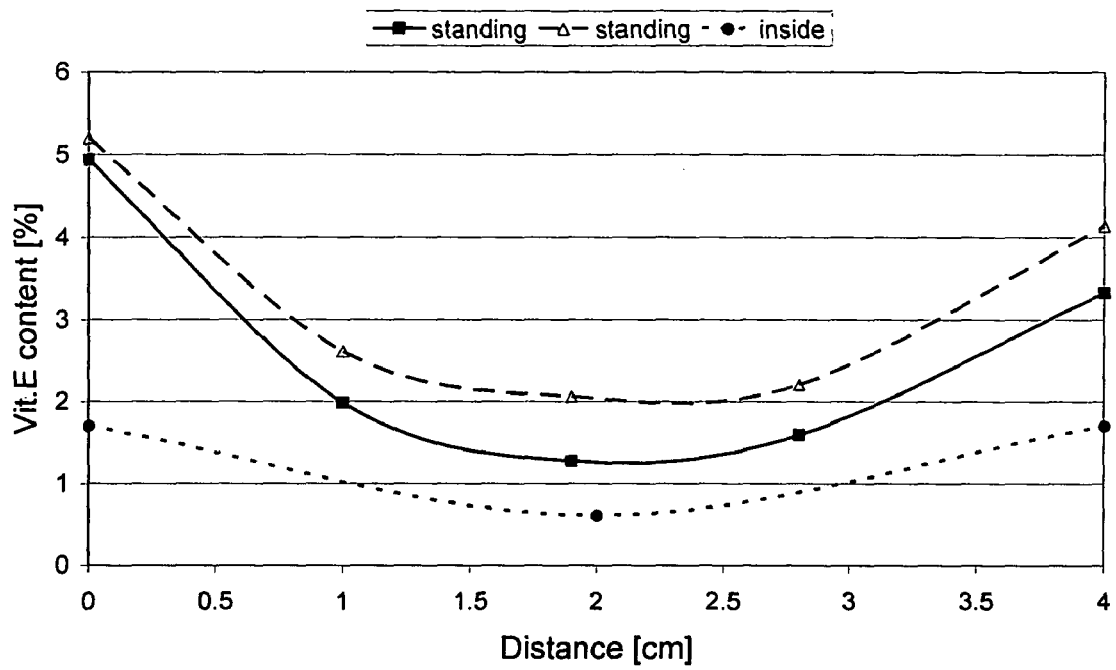
Figure 5: Vitamin E concentration profiles in the sintered blocks that were previously Compacted and soaked in a Vitamin E-hexane solution. 2 blocks were standing in the solution, partially immersed in the fluid and 1 block was completely immersed in the fluid (inside).
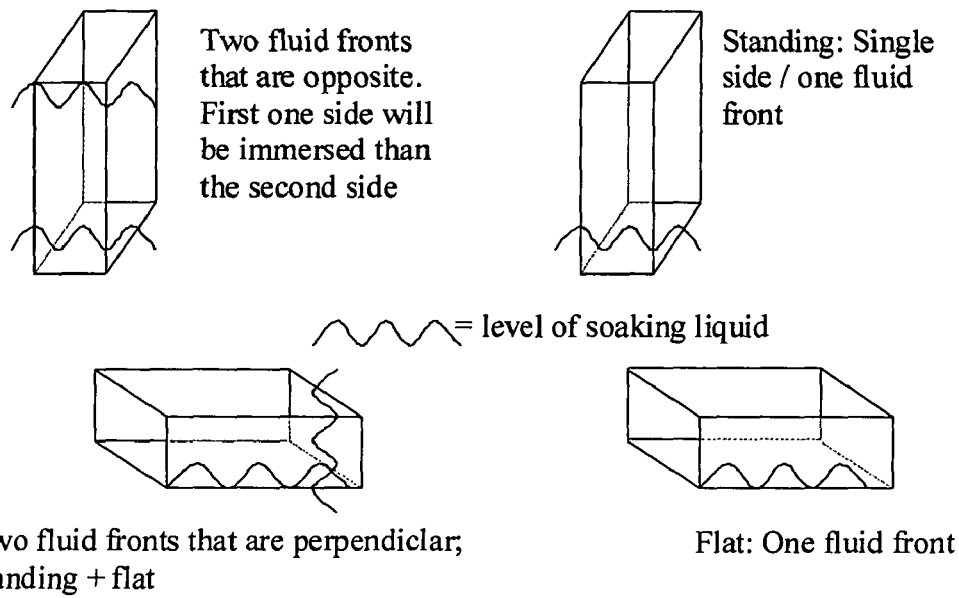
Figure 6: Examples of one or more soaking steps with different soaking directions.

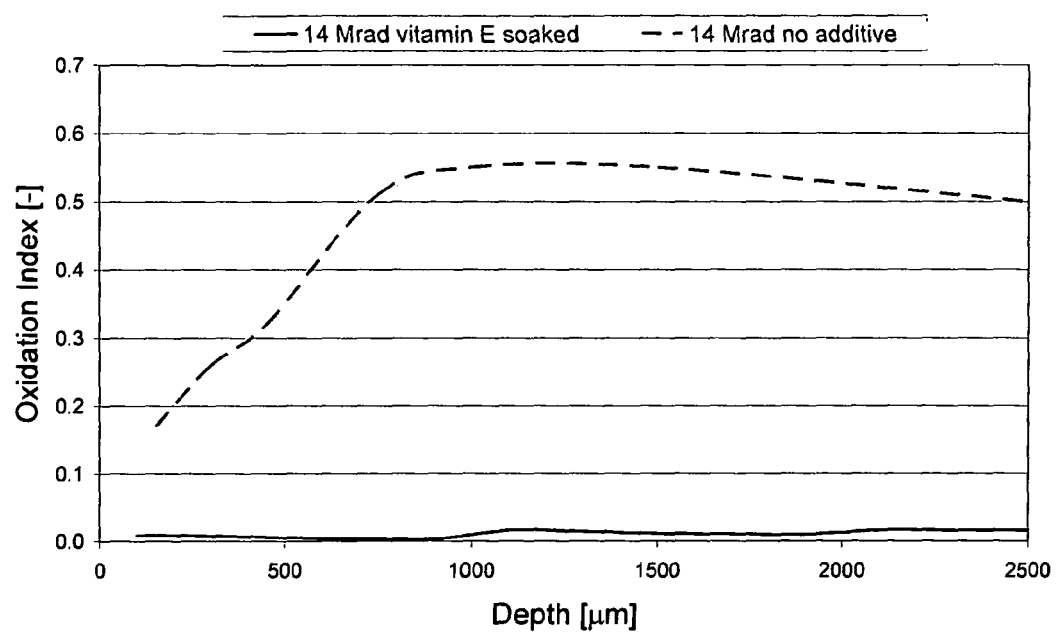
Figure 7: Oxidation profiles of vitamin E soaked and additive-free samples, both gamma irradiated with a dose of 14 Mrad in air (no post-irradiation thermal treatment).

COMPOSITIONS AND METHODS OF MAKING COMPOSITIONS

This is a U.S. National Phase Application filed under 35 U.S.C. §371 from PCT Application International Number PCT/EP2009/005028, International Publication Number WO 2010/003688, International Filing Date 10 Jul. 2009, claiming priority to Great Brittan Application Number 0812890.2, filed 11 Jul. 2008. Each of the above references and all others cited in this application are hereby incorporated herein by reference in their entireties.

The present invention relates to a method for obtaining a composition/mixture of at least two components. The present invention also relates to compositions/mixtures made by such methods, and devices incorporating such compositions/mixtures.

Ultra High Molecular Weight Polyethylene (UHMWPE) is a versatile material combining high strength and toughness with high wear resistance. As a result, it is used in many industrial applications such as bearings, gearings, liners, chain guides, for example. A problem with processing UHMWPE results from its extremely high melt viscosity (zero shear viscosity>$10^8$ Pa·s), which does not enable for common processing techniques such as injection molding or extrusion. Instead, UHMWPE powder is sintered and then the part is mechanically machined into the desired shape. Since conventional melt-processing and mixing techniques are not applicable, blending of additives is normally done by mixing the UHMWPE powder with the additive followed by sintering. The mixing of the two powders is difficult since the UHMWPE powder has a very low density and is highly porous. If the additive is also a powder, it is difficult to form a homogeneous powder mixture. If the additive is in liquid form, homogeneous distribution of that liquid in the powder having an extremely high surface area is also difficult.

It is known to mix additives with the UHMWPE powder or diffuse them into the UHMWPE powder before the sintering step. It is also known to diffuse the additives into the sintered products.

According to a first aspect of the present invention, there is provided a method for obtaining a composition of at least two components, comprising the steps of:
providing at least one first fluid component;
providing at least one second solid component and processing it so that the first component can diffuse into the second component; and
diffusing the first component into the second component.

The first component may comprise at least one liquid.

The first component may comprise at least one gas.

The first component may comprise at least one solid dissolved in the fluid.

The second component may be processed so that capillary forces are created or increased when the first component contacts the second component.

The second component may be processed so that capillaries (conduits/channels) are formed to generate or increase capillary forces for the first component that contacts the second component.

The second component may be a powder. The powder may be compacted. The powder may be compacted so that capillary forces are created or increased for the first component that contacts the second component.

The compacted powder block may be soaked in at least one liquid. The liquid may be a pure additive. The liquid may be a solution comprising the additive.

The method may further comprise the step of treating the composition so that liquid or gas is removed to produce a solid composition.

The compacted powder block may be treated so that the solvent evaporates leaving the additive in the compacted block.

The method may further comprise the step of sintering the composition.

The second component may be a polymer. The polymer may be a co-polymer.

The compacted block may be sintered above the melting temperature of the polymer.

The polymer may be crystalline. The polymer may be semi-crystalline.

The polymer may be selected from the group consisting of polyolefins (polyethylene, polypropylene), polyoxymethylene (POM), polyamides (PA6, PA6.6, PA4.6), PVC, PEEK, PPSU, polytetrafluoroethylene (PTFE) and polyesters (PET, PBT, PEN, PC).

The polymer may be selected from the group consisting of UHMWPE, HDPE, LDPE and LLDPE.

The polymer may be polyethylene having a molecular weight of at least 100,000. The polyethylene may have a molecular weight of at least 300,000. The polyethylene may have a molecular weight of at least 1 million.

The polymer may be amorphous.

The polymer may be selected from the group consisting of polystyrene or modified styrene polymers (SAN, SB, ABS), PMMA, polyacrylates (for example polybutylacrylate), PPO.

The method may further comprise the step of cross-linking the polymer.

The cross-linking may be performed after sintering the composition.

The cross-linking may be performed by irradiation. The cross-linking may be performed using gamma or e-beam irradiation.

The cross-linking may be performed by a chemical species. The chemical cross-linking species may be dibenzoylperoxide.

The first component may comprise a chemical species for cross-linking the polymer.

The first component may comprise an antioxidant.

The first component may comprise at least one Vitamin.

The first component may comprise Vitamin E.

The first component may comprise an antibiotic.

The antibiotic may be selected from the group consisting of gentamycin, vancomycin, streptomycin, penicillin and derivatives thereof.

The first component may comprise a foaming agent. That is, a solvent with a boiling temperature above the sintering temperature of the polymer.

The first component may comprise a reactive monomer.

The first component may comprise an initiator to start a polymerization of a monomer.

The reactive monomer may be selected from the group consisting of ethylene, propylene, vinyl chloride, oxymethylene, butylacrylate, methyl methacrylate, and styrene.

The first component may comprise a dye. The dye may be natural. The dye may be synthetic.

The dye may be selected from the group consisting of fuchsin, Sudan red, Sudan black, anthraquinone, azo compounds, sulphuric compounds, natural dyes such as carotene, curcumin (turmeric) or carmine.

The first component may comprise a clarifying or nucleating agent such as sorbitol based compounds (DBS, MDBS, DMDBS), sodium benzoate, talc or thymine.

The first component may be diffused into the second component in at least two stages.

The composition may be sterilised.

The composition may be formed into an artefact.

The artefact may be a medical device.

The medical device may be sterilised.

According to a second aspect of the present invention, there is provided a composition prepared by any of the methods according to the first aspect of the present invention.

According to a third aspect of the present invention, there is provided a composition comprising a compacted powder according to the first aspect of the present invention.

Preferably, the compacted powder is prepared in such a way that capillary forces are created or increased for a fluid component that contacts the compacted powder.

According to a fourth aspect of the present invention, there is provided a composition comprising at least one first fluid component and at least one second solid component according to the first aspect of the present invention, wherein the first component is distributed within the second component.

According to a fifth aspect of the present invention, there is provided a composition comprising a compacted powder and at least one fluid component according to the first aspect of the present invention.

According to a sixth aspect of the present invention, there is provided a composition comprising at least one first fluid component and at least one second solid component according to the first aspect of the present invention, wherein the first component is distributed within the second component, and wherein the composition is sintered.

According to some embodiments of the present invention, the additives are diffused into the compacted body, i.e., into the intermediate state between powder and sintered object. During compaction below the melting temperature, the porous powder particles are deformed into a dense body but since no melting occurs, the particles are not completely fused. Between the deformed particles, there are very narrow channels that support the rapid and uniform fluid absorption due to the capillary forces acting locally. These capillary forces are not present between loose particles or in the sintered and completely fused product. After the additive has been soaked into the compacted body, a final sintering step is done to fuse the particles. Viscous or solid additives can be dissolved to enable soaking into the compacted body. For these embodiments, the solvent can be evaporated before sintering or it evaporates during the subsequent sintering step.

The sintered materials can be used for medical implants such as total hip or knee replacements. These polyethylene implants containing additives for anti-oxidative purposes can also be cross-linked after the pre-compaction-soaking-sintering process using gamma or e-beam irradiation. The irradiation doses may vary from 1 to 25 Mrad or more preferably from 3 to 20 Mrad. The medical implants can also be sterilized either using gamma irradiation (2.5-4 Mrad) or surface sterilization methods such as ETO or gas plasma treatments.

Solid compositions may be processed from any type of polymer in powder form or from more than one type of polymer. If a polymer is available only in solid bulk or pellet form, the material may be grinded to a powder prior to compaction. The pressure may be chosen between 0-50 MPa, more preferably between 0-20 MPa and even more preferably between 5-15 MPa. The processing temperature is preferably set to a temperature below the melting temperature ($T_m$) of the polymer. If two or more different polymers are processed the temperature is preferably set to a temperature below $T_m$ of the polymer with the lowest $T_m$. More preferably, the temperature is set to $T_m$-30° C., more preferably to $T_m$-20° C. and even more preferably to $T_m$-10° C. The pressure may be applied first followed by heating of the mould. The heating of the mould may be applied first followed by the application of pressure. The compaction time depends on the volume of the solid composition and is preferably between 1 second and 100 hours, more preferably between 1 minute and 24 hours and even more preferably between 30 minutes and 6 hours. All material in the processing mould should reach the desired compaction time. The temperature may be decreased prior to releasing the pressure. The pressure may be released prior to decreasing the temperature. The compaction procedure may be performed in normal air atmosphere, in vacuum environment or in an inert gas atmosphere such as nitrogen or argon.

In those embodiments of the invention comprising polyethylene, compaction of the polyethylene may be performed at a temperature above room temperature and below the melting temperature (25-130° C.), at pressures ranging from 0.5-25 MPa (more preferably 1 to 15 MPa, even more preferably 2 to 10 MPa).

Compacted solid compositions are preferably processed from UHMWPE. For example, UHMWPE powder may be filled in a mould at room temperature and subsequently a pressure of about 10 MPa applied and maintained during the whole compaction procedure. Subsequently, the temperature is increased from room temperature to about 120° C. At about 120° C. and about 10 MPa, the powder is kept for a period of time to completely heat all of the polymer powder to about 120° C. The period of time depends on the volume of the solid composition, for example around 20 minutes for a composition with the dimensions 4×4×2 cm, and around 4 hours for a composition with the dimensions 20×20×5 cm. Subsequently, the temperature is decreased. Below a temperature of about 50° C., the pressure can be released and the solid composition can be removed from the mould.

Reference will now be made, by way of example, to the following drawings and examples, in which:

FIG. 1 shows soaking of a compacted GUR 1020 block in a red isopropanol/fuchsin solution;

FIG. 2 shows soaking of a sintered GUR 1020 block in a red isopropanol/fuchsin solution;

FIG. 3 shows compacted and soaked blocks cut into two pieces (1% curcumin solution in acetone) after drying;

FIG. 4 shows average weight change of the 2 standing blocks as a function of the soaking time;

FIG. 5 shows vitamin E concentration profiles in the sintered blocks that were previously compacted and soaked in a Vitamin E-hexane solution;

FIG. 6 shows examples of one or more soaking steps with different soaking directions; and FIG. 7 shows oxidation profiles of Vitamin E soaked and additive-free samples.

EXAMPLE 1

Diffusion of Dyes/Colors into Compacted UHMWPE Bodies

GUR 1020 UHMWPE powder was compacted in a press at 120° C. and a pressure of 10 MPa. A small block (4 cm×3 cm×5 cm) was cut from the plate and put into a glass containing 75 ml of isopropanol and 0.04 grams of Fuchsin (Merck). In FIG. 1, the soaking behavior at room temperature of the pre-compacted block is depicted as a function of time. Within seconds, the fluid including the color additive is absorbed and within an hour the body is uniformly colored.

FIG. 1 shows soaking of a compacted GUR 1020 block in a red isopropanol/fuchsin solution (left: seconds after immersion; middle: 30 minutes after immersion; right: 1 hr after immersion).

COMPARATIVE EXAMPLE 1

A sintered block of GUR 1020 (4×3×5 cm) was put into a glass containing 75 ml of isopropanol and 0.04 grams of Fuchsin (Merck). FIG. 2 shows the soaking behavior at room temperature of the block depicted as a function of time (left: seconds after immersion; middle: 30 minutes after immersion; right: 1 hr after immersion).

In the comparative example, the sintered block is not impregnated with the fluid.

EXAMPLE 2

Soaking of Natural Additives/Antioxidants into Small Compacted Blocks

GUR 1020 blocks were compacted below the melting temperature at 120° C. in a laboratory scale press for 15 minutes at 10 MPa. Afterwards, the compacted blocks were rapidly cooled to room temperature.

Soaking: 3.8×4×1.5 cm compacted blocks were soaked at room temperature in a 1% w/w solution of acetone containing curcumin as an additive. After soaking for an hour, the acetone was evaporated in a vacuum oven at 40° C. for 24 hr. The compacted and soaked block was cut into two pieces (FIG. 3) showing the homogeneous distribution of the yellow curcumin FIG. 3 shows compacted and soaked blocks cut into two pieces (1% curcumin solution in acetone) after drying. FIGS. 3 (*a*) and (*b*) represent two different blocks, both cut into 2 pieces

EXAMPLE 3

Soaking of Antioxidants—Vitamin E into Small Compacted Blocks Followed by Sintering The compaction was done as described in Example 2. After compaction the samples were immersed in a hexane-vitamin E solution (2.8% w/w) and the weight was measured during soaking. 2 compacted blocks were standing in the solution (only lower part of block immersed, see also FIG. 1) and 1 block was completely covered with the soaking solution (inside the liquid).

After soaking, the samples were dried to constant weight in a vacuum oven (see example 2) and the weight was measured again to determine the VitE content in the material. Finally, the compacted polyethylene blocks were sintered for 15 minutes in a mold at a temperature of 220° C. and a pressure of 5 MPa. The samples were finally cooled rapidly (in 8 minutes) to room temperature.

FTIR measurements were conducted to determine the content of vitamin E in the samples. From the sintered blocks, small portions were cut in regular distances. From these smaller pieces, microtome slices were produced with a thickness of about 300 microns (or 5 times 60 microns). Of these slices, FTIR spectra were recorded with a Bruker Vertex 70 with a resolution of 4 cm$^{-1}$ and a total of 16 scans.

For a more precise determination of the vitamin E concentration, the measured spectra were normalized and a spectrum of pure UHMWPE was deducted. The 2020 cm$^{-1}$ peak was chosen as reference peak and its height (relative to the height at 2100 cm$^{-1}$ and 1980 cm$^{-1}$) was normalized to an absorbance of 0.05. This is supposed to correspond to a film thickness of 100 microns. Of this normalized spectrum, the spectrum of pure UHMWPE, normalized by the same procedure, was deducted. Then, the height of the C-OH absorption (vitamin E peak) at 1210 cm$^{-1}$ (relative to the height at 1188 cm$^{-1}$ and 1231 cm$^{-1}$) was determined. The concentration of vitamin E (mol/kg) was calculated according to the following equation:

$$A = \epsilon \cdot b \cdot C$$

A=peak absorbance (height of the 1210 cm$^{-1}$ peak)
$\epsilon$: molar absorbivity of the $\alpha$-tocopherol —OH in UHMWPE (in kg·cm$^{-1}$·mol$^{-1}$).
Experimentally determined=133 kg·cm$^{-1}$·mol$^{-1}$
b=path length (film thickness) in cm=0.01 cm for normalized spectra
C=concentration of $\alpha$-tocopherol in UHMWPE in mol·kg$^{-1}$ In FIG. 4, the average weight change of the 2 standing blocks is depicted as a function of the soaking time. Initially there is a fast weight increase within 4 hrs, afterwards, the weight increase levels off. The weight increase is due to the absorption of the hexane-vitamin E solution.

In FIG. 5, the concentration profiles of Vitamin E in the blocks are shown after solvent evaporation and subsequent sintering. FIG. 5 shows vitamin E concentration profiles in the sintered blocks that were previously compacted and soaked in a Vitamin E-hexane solution. 2 blocks were standing in the solution, partially immersed in the fluid, and 1 block was completely immersed in the fluid (inside).

The weight % of Vitamin E in the UHMWPE determined from the integrated FTIR spectra and from the gravimetric method are listed below.

|  | Gravimetric | Integrated FTIR data |
|---|---|---|
| Standing #1 | 3.1% | 2.3% |
| Standing #2 | 3.1% | 2.9% |
| Inside | 0.81% | 1.15% |

This example shows that it is possible to impregnate the compacted body with a solution containing Vitamin E, subsequently evaporate the solvent (hexane) and finally sinter the compacted material. The amount of vitamin E in the block can be tuned by selecting different concentrations of Vitamin E in the solution or by selecting the appropriate soaking procedure.

In accordance with embodiments of the present invention, compacted blocks can be soaked in more than one soaking step. The additive in the fluid during a second or third soaking step may be different from the first soaking step. The additive can also be a chemical cross-linking agent (such as dibenzoylperoxide) or an antibiotic (such as gentamycin) or a reactive monomer (e.g. styrene or methylmethacrylate) or a foaming agent (a solvent with boiling temperature above the sintering temperature of the polyethylene). The foaming agent can have a high boiling temperature at ambient pressure, i.e. after sintering but the foaming agent may also be liquid during sintering at elevated pressures and be in the gaseous phase upon release of the pressure after sintering. Also the direction of the soaking can be different as explained in FIG. 6, which shows examples of one or more soaking steps with different soaking directions.

The soaking can be also restricted to a part of the compacted object therewith creating portions in the block that contain the additive and portions without the additive. In example 1, if the compacted block was removed from the soaking fluid (left picture) the sintered product would only be partially colored. This results in portions of blended and virgin material in the compacted body. Also a compacted and soaked body with an additive can be placed in a solvent in a second step to locally extract an additive and create concentration gradients in the compacted material.

The current invention is not restricted to UHMWPE powders but also powders from lower molecular weight polyethylenes such as HDPE, LDPE, LLDPE. The method can also be applied to other polymers such as PMMA, polystyrene, polypropylene, PVC, polyoxymethylene (POM), PPSU, PPO, PEEK, Polyamides (PA6, PA 6.6, PA 4.6), other polyacrylates (such as poly butylacrylate), PTFE.

Advantages of the present method include the following. For additive mixing involving powders, the capillary forces acting in the compacted body are not present between loose particles and therefore it is not possible to get a rapid, uniform and efficient fluid uptake for fluid additives. For solid additives, the present method enables a more uniform distribution of the additives by first dissolving the additive and subsequent soaking. Of course, solid additives cannot be soaked/diffused into the compacted body without the use of a carrier liquid.

For additive diffusion into sintered objects, the particles in the sintered objects are fused and no capillary forces are acting between the particles that enable a rapid and efficient fluid absorption and diffusion (see comparative example 1).

Therefore, elevated temperatures close to the melting temperature are necessary to stimulate the classical Fick diffusion into the object which is slower and less efficient. In the present invention, additives are soaked into compacted materials at room temperature within minutes/hours which is not possible when using sintered UHMWPE parts.

EXAMPLE 4

Oxidation of Blocks Soaked with Antioxidant and Irradiated with Gamma Radiation

The oxidation resistance of a block containing antioxidants that was gamma irradiated was determined. A block that was processed according to the method described in Example 3 (soaked with vitamin E prior to sintering) was irradiated with a dose of 14 Mrad (±10%) in normal air atmosphere. No post-irradiation thermal treatment was applied.

Cylindrical samples with a length of 40 mm and a diameter of 10 mm were drilled out of the irradiated block. Subsequently, the samples were accelerated aged according to ASTM F 2003 in an oxygen bomb at 5 atm oxygen pressure and 70° C. for 14 days. Oxidation indices of the aged components were determined by means of FTIR according to ASTM F 2102-06. The method for making measurements of the oxidation index according to this standard is as follows: thin slices of the sample are made with a microtome and tested to give a depth profile for the oxidation index. From the micro-slices taken of the sample the infrared spectrum is taken by means of FTIR with a resolution of 4 cm$^{-1}$. The oxidation index is defined as the intensity of the peaks in the region 1680-1765 cm$^{-1}$, which is associated with carbonyl peaks, divided by the intensity in a reference band which lies between 1330 and 1396 cm$^{-1}$.

In FIG. 7, the oxidation profile of a vitamin E soaked and irradiated (gamma in air, 14 Mrad) sample is shown. The oxidation profile is an average of three individual measurements. As control sample, an UHMWPE without additive, irradiated with 14 Mrad in air (without post-irradiation thermal treatment), is shown. The reduced oxidation of the material that was soaked with vitamin E is clearly demonstrated, as the maximum oxidation index of this material is below 0.02.

The invention claimed is:

1. A method for obtaining UHMWPE containing at least one component comprising:
    providing UHMWPE in the form of a powder;
    compacting the UHMWPE at a temperature below the melting temperature of the UHMWPE and at a pressure greater than atmospheric pressure, for a time, temperature, and pressure sufficient to form at least a first dense body comprising deformed porous powder particles formed from UHMWPE, wherein the deformed porous powder particles of the first dense body are not completely fused and comprise narrow channels throughout the first dense body, wherein the narrow channels are capable of supporting rapid and uniform liquid adsorption into the first dense body due to capillary forces in the narrow channels;
    providing at least a first component as a liquid;
    exposing at least a portion of the first dense body to the first component as a liquid, wherein the liquid is drawn into the first dense body by capillary forces in the narrow channels of the first dense body thereby forming a composition comprising UHMWPE and the at least first component.

2. The method of claim 1, wherein the first component is in solution in a liquid, consisting of
    exposing the first component in solution in a liquid to at least a portion of the first dense body, wherein the first component in solution in the liquid is drawn into the first dense body by capillary forces in the narrow channels of the first dense body acting on the liquid and thereby carrying the first component into the first dense body thereby forming a composition comprising UHMWPE, the first component, and the liquid.

3. The method of claim 2, further comprising removing the liquid from the first dense body while the first component remains in the first dense body and is removed from the liquid solution, thereby forming a composition comprising UHMWPE and the first component.

4. The method of claim 3, wherein the liquid is removed from the first dense body by heating the first dense body to a temperature below the melting temperature of the UHMWPE.

5. The method of claim 3, wherein the UHMWPE contains at least a first and a second component, comprising
    exposing the first dense body comprising UHMWPE and the first component to a second component in solution in a liquid, whereby the second component in the solution is drawn into the first dense body by capillary forces in the narrow channels of the first dense body acting on the liquid and thereby carrying the second component into the first dense body, thereby forming a composition comprising UHMWPE, the first and second components, and the liquid of the solution of the second component.

6. The method of claim 5, further comprising removing the liquid from the first dense body while the second component remains in the first dense body and is removed from the liquid solution, thereby forming a composition comprising UHMWPE and the first and second components.

7. The method of claim 6, wherein the liquid is removed from the first dense body by heating the first dense body to a temperature below the melting temperature of the UHMWPE.

8. The method of claim 1, wherein the compacting pressure is about 2 to about 15 MPa.

9. The method of claim 1, wherein the compacting pressure is about 10 MPa.

10. The method of claim 1, wherein the compacting temperature is about 10° C. less than the melting temperature of the UHMWPE.

11. The method of claim 1, wherein the compacting temperature is about 120° C.

12. The method of claim 1, further comprising sintering the composition.

13. The method of claim 12, wherein the sintering comprises heating the compacted first dense body in a compaction mold at a temperature of about 220° C. and a pressure of about 5 MPa for a time sufficient to sinter the first dense body.

14. The method of claim 13, wherein the sintering is performed for about 15 minutes.

15. The method of claim 2, further comprising sintering the composition.

16. The method of claim 15, wherein the sintering comprises heating the compacted first dense body in a compaction mold at a temperature of about 220° C. and a pressure of about 5 MPa for a time sufficient to sinter the first dense body.

17. The method of claim 16, wherein the sintering is performed for about 15 minutes.

18. The method of claim 5, further comprising sintering the composition.

19. The method of claim 18, wherein the sintering comprises heating the compacted first dense body in a compaction mold at a temperature of about 220° C. and a pressure of about 5 MPa for a time sufficient to sinter the first dense body.

20. The method of claim 19, wherein the sintering is performed for about 15 minutes.

21. The method of claim 6, further comprising sintering the composition.

22. The method of claim 21, wherein the sintering comprises heating the compacted first dense body in a compaction mold at a temperature of about 220° C. and a pressure of about 5MPa for a time sufficient to sinter the first dense body.

23. The method of claim 22, wherein the sintering is performed for about 15 minutes.

24. The method of claim 1, further comprising crosslinking the composition.

25. The method of claim 24, further comprising crosslinking the composition by irradiation.

26. The method of claim 24, wherein the crosslinking is performed by gamma irradiation of about 2.5 to about 4 Mrad or by e-beam irradiation of about 3 to about 20 Mrad.

27. The method of claim 2, further comprising crosslinking the composition.

28. The method of claim 27, further comprising crosslinking the composition by irradiation.

29. The method of claim 27, wherein the crosslinking is performed by gamma irradiation of about 2.5 to about 4 Mrad or e-beam irradiation of about 3 to about 20 Mrad.

30. The method of claim 5, further comprising crosslinking the composition.

31. The method of claim 30, further comprising crosslinking the composition by irradiation.

32. The method of claim 30, wherein the crosslinking is performed by gamma irradiation of about 2.5 to about 4 Mrad or e-beam irradiation of about 3 to about 20 Mrad.

33. The method of claim 6, further comprising crosslinking the composition.

34. The method of claim 33, further comprising crosslinking the composition by irradiation.

35. The method of claim 33, wherein the crosslinking is performed by gamma irradiation of about 2.5 to about 4 Mrad or e-beam irradiation of about 3 to about 20 Mrad.

36. The method of claim 1, wherein the first component comprises an antioxidant.

37. The method of claim 36, wherein the antioxidant comprises vitamin E.

38. The method of claim 1, wherein the first component comprises an antibiotic.

39. The method of claim 1, wherein the first component comprises a foaming agent.

40. The method of claim 1, wherein the first dense body comprising UHMWPE and at least a first component is used in the manufacture of a medical device.

41. The method of claim 1, wherein the first dense body comprising UHMWPE and at least a first component is used in the manufacture of a medical implant selected from the group consisting of hip and knee replacements.

42. The method of claim 2, wherein the first dense body comprising UHMWPE and at least a first component is used in the manufacture of a medical device.

43. The method of claim 2, wherein the first dense body comprising UHMWPE and at least a first component is used in the manufacture of a medical implant selected from the group consisting of hip and knee replacements.

44. The method of claim 5, wherein the first dense body comprising UHMWPE and at least a first and a second component is used in the manufacture of a medical device.

45. The method of claim 5, wherein the first dense body comprising UHMWPE and at least a first and a second component is used in the manufacture of a medical implant selected from the group consisting of hip and knee replacements.

46. The method of claim 6, wherein the first dense body comprising UHMWPE and at least a first and a second component is used in the manufacture of a medical device.

47. The method of claim 6, wherein the first dense body comprising UHMWPE and at least a first and a second component is used in the manufacture of a medical implant selected from the group consisting of hip and knee replacements.

48. The method of claim 1, wherein the first dense body comprising UHMWPE and at least a first component is used in the treatment of a medical condition using a medical implant selected from the group consisting of hip or knee replacements wherein the medical implant comprises the first dense body comprising UHMWPE and at least a first component.

49. The method of claim 2, wherein the first dense body comprising UHMWPE and at least a first component is used in the treatment of a medical condition using a medical implant selected from the group consisting of hip or knee replacements wherein the medical implant comprises the first dense body comprising UHMWPE and at least a first component.

50. The method of claim 5, wherein the first dense body comprising UHMWPE and at least a first and a second component is used in the treatment of a medical condition using a medical implant selected from the group consisting of hip or knee replacements wherein the medical implant comprises the first dense body comprising UHMWPE and at least a first and a second component.

51. The method of claim 6, wherein the first dense body comprising UHMWPE and at least a first and a second component is used in the treatment of a medical condition using a medical implant selected from the group consisting of hip or knee replacements wherein the medical implant comprises the first dense body comprising UHMWPE and at least a first and a second component.

* * * * *